United States Patent [19]

Paar et al.

[11] Patent Number: 4,544,715

[45] Date of Patent: Oct. 1, 1985

[54] HARDENING COMPONENTS FOR PAINT BINDERS

[75] Inventors: Willibald Paar; Rudolf Schipfer, both of Graz, Austria

[73] Assignee: Vianova Kunstharz, A.G., Werndorf, Austria

[21] Appl. No.: 621,269

[22] Filed: Jun. 18, 1984

[30] Foreign Application Priority Data

Jun. 20, 1983 [AT] Austria ................................ 2258/83

[51] Int. Cl.$^4$ .............................................. C08L 63/02
[52] U.S. Cl. ................................. 525/528; 204/181.7; 523/414; 523/415; 524/901; 525/510; 525/529; 525/533; 528/73
[58] Field of Search ............... 525/528, 529, 533, 510; 524/901; 523/415, 414; 528/230, 249, 73

[56] References Cited

U.S. PATENT DOCUMENTS

| | | |
|---|---|---|
| 2,517,128 | 8/1950 | Meunier et al. ...................... 528/249 |
| 3,725,350 | 4/1973 | Hunsucker ........................... 528/249 |
| 3,773,730 | 11/1973 | Hunsucker ........................... 528/249 |

*Primary Examiner*—Theodore E. Pertilla
*Attorney, Agent, or Firm*—A. W. Breiner

[57] ABSTRACT

Hardener components which crosslink through transesterification comprising (A) a KNOEVENAGEL reaction product of a carbonyl compound and a compound such as the diester of malonic acid reacted in a MICHAEL-addition reaction with (B) a substituted oxazolidine carrying a secondary amino group, and where the reaction product of (A) and (B) is thereafter reacted through the methylene groups with (C) a polyisocyanate is described. The hardener components are particularly suitable for use in water-dilutable cationic paint binders.

10 Claims, No Drawings

HARDENING COMPONENTS FOR PAINT BINDERS

FIELD OF INVENTION AND BACKGROUND

The present invention is directed to a process for producing improved hardening components for paint binders. More particularly, this invention relates to a process for producing paint binders which can be crosslinked by transesterification.

European Patent Application EP No. 00 12 463 A 1 describes heat-hardenable binder compositions which crosslink on stoving in the presence of a transesterification catalyst through transesterification of the hydroxy groups of a resin component, which is free from acid groups and ethylenically unsaturated groups, with a polyester, which is free from acid groups and carrying more than one β-hydroxy group. As long as the resin component is a cationic water-dilutable resin, the binder system may be applied by electrodeposition. The introduction of the β-hydroxy ester group, particularly favorable for transesterification reactions, onto the resin component according to this European patent application, is effected through reaction of a polycarboxylic acid anhydride with glycols, glycol monoethers, polyols, and/or, preferably, with monoepoxides. The preferred polyesters carrying β-hydroxy groups are those prepared from trimellitic acid anhydride and a glycidyl ester of a saturated aliphatic carboxylic acid with from 9–11 C-atoms, the carboxy groups thereof being linked to a tertiary carbon atom, known as "glycidylester C 10 E" in the literature. On crosslinking of the aforesaid component, the glycols linked as β-hydroxy esters are set free at stoving temperatures of between 150° and 200° C., and are thus eliminated from the coating. In addition to the relatively high stoving temperatures necessary for reaction even when using transesterification catalysts, the relatively high quantity of decomposition products is a serious disadvantage of the aforesaid type of crosslinking component. Furthermore, high-quality paint raw materials are split off and have to be eliminated from the paint film. This is a drawback for economical as well as for ecological reasons.

European Patent Application EP-Al No. 00 82 291, therefore, proposes to esterify the carboxy groups of crosslinking components with low molecular weight alcohols. The carboxy groups stem from special dicarboxylic acids, particularly of malonic acid. These dicarboxylic acid esters may be chain ends of oligomeric or polymeric esters. It has now been found that hardening components carrying, in addition to the malonic ester structure, a basic function in the form of an oxazolidine group provide particularly favorable properties when applied as cathodic electrodisposition (CED) paints. These hardening components have no saponifiable ester groups other than the functional ester structures.

Accordingly, the present invention is directed to a process for producing crosslinking components suitable for water-dilutable cationic paint binders which will crosslink through transesterification, and to the binders obtained, characterized in that (A) A KNOEVENAGEL reaction product of a carbonyl compound and a compound of the general formula $$X-CH_2-Y$$

wherein

X is —COOR, —CN or —COCH$_3$,

Y is —COOR, and

R is an alkyl radical having from 1–4 C-atoms, is reacted in a MICHAEL-addition reaction at from 50° to 100° C. with (B) A substituted oxazolidine carrying a secondary amino group, of the general formula

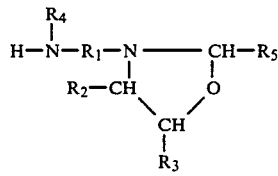

wherein $R_1$ is a straight chain or branched or cyclic alkylene radical with from 2–12 C-atoms or an aralkylene radical, $R_2$ is a hydrogen atom or a methyl group, $R_3$ is a hydrogen atom or an alkyl radical, $R_4$ is the radical of an acrylic or methacrylic monomer monofunctional with regard to the double bond and remaining after reaction with an active hydrogen atom, $R_5$ is a hydrogen atom or an alkyl radical with from 1–12 C-atoms or an aryl radical optionally substituted, and the reaction product of (A) and (B) is reacted at 30° to 35° C. via the active methylene groups with (C) A a di- or polyisocyanate, the quantity of isocyanate groups corresponding to the active methylene groups of the oxazolidine rings.

In step (A) an aldehyde or ketone is reacted in a KNOEVENAGEL-reaction with a CH-acidic ester. This reaction between methyl components with high C-H-acidity and carbonyl compounds is described, for example, in *Organikum*, 12th edition, VEB Deutscher Verlag der Wissenschaften, Berlin 1973, pages 508 ff. (see also *Rompp Chemie Lexikon*, 7th edition).

The present invention is also directed to the use of the crosslinking components of this invention for crosslinking hydroxy- and amino-functional based resins; and to the use of such resin-hardener systems as binders for cathodic electrodeposition.

The following reaction mechanisms are theorized for the process of the invention:

(A) KNOEVENAGEL-Reaction Product

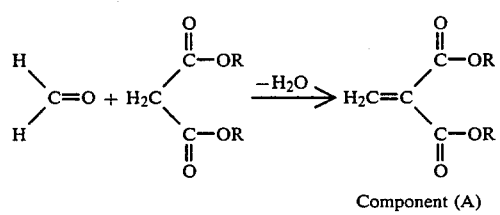

Component (A)

(B) MICHAEL-Addition

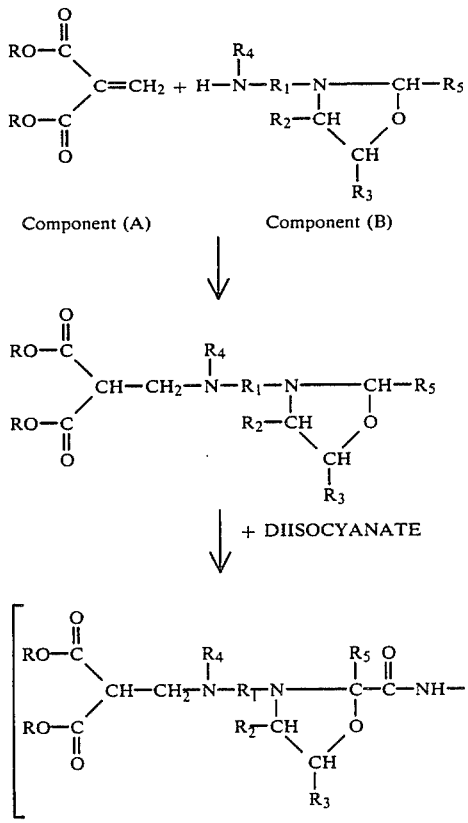

Component (A)      Component (B)

+ DIISOCYANATE (C)

wherein
$R_1$ through $R_5$ are as above defined, and
$R_6$ is an aromatic, aliphatic, or cycloaliphatic hydrocarbon radical.

As can be seen from the formula for the crosslinking components prepared according to the present invention, these components have essential advantages over the products of the art, as follows:

(a) Other than for the functional ester groups, the system carries no groups which are prone to split, and thus cause an essential reduction in molecular weight.

(b) The basic groups are of ionic structure equal to those of the cationic basic resin, thus on cathodic electrodeposition, equivalent deposition is guaranteed.

(c) The possibility of selecting radicals $R_1$ and $R_4$ permits plastification of the hardener molecule, and thus for the entire system. Accordingly, the surface quality of the deposited films and the flexibility of the stoved coatings can be monitored.

(d) The presence of acid amide groups essentially enhances the adhesion of the films.

(e) The oxazolidine groups improve pigment wetting of the binder system and emulsifying characteristics of the resin component and other additives.

The preferred starting materials for use in preparing component (A) of this invention are the diesters of malonic acid with $C_1$-$C_4$ alkanols, such as dimethylmalonate, diethylmalonate, n- or iso-propylmalonate, n-, iso- or tertiary butylmalonate, and diethylmethylmalonate. In the same reaction, alkyl- or cycloalkylesters of cyano-acetic acid, such as the methyl, ethyl, propyl, butyl, cyclopentyl- or cyclohexylesters, can be used as well as the methyl or ethyl esters of acetoacetic acid. The preferred aldehyde for use in preparing component (A) of this invention is formaldehyde, particularly in the form of its polymerized form (paraformaldehyde). In principle, higher aldehydes, for example acetaldehyde or a butanal, or an aromatic aldehyde, can be used but provide no special advantage. Furthermore, ketones such as methylisobutylketone can be employed. Component (A) can be prepared according to an alternative of the KNOEVENAGEL process wherein the reaction water is azeotropically removed, at times referred to as the COPE alternative. Thus, in a preferred embodiment the paraformaldehyde is added in portions to the ester at 60° to 70° C. and dissolved therein. Optionally, as a catalyst for the reaction, a blend of piperidine and formic acid at a level of about 1 mole-% is added. The reaction temperature should not surpass 90° C. until the paraformaldehyde has dissolved completely. Subsequently, the temperature is slowly raised and the reaction water which forms is distilled off at 120° to 150° C. by azeotropic distillation with an entraining agent, for example an aliphatic or aromatic hydrocarbon. The reaction is monitored via the quantity of reaction water which is formed.

The substituted oxazolidine used in step (B) carries one secondary amino group and has the general formula

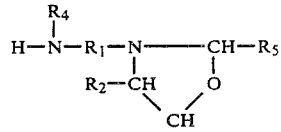

wherein the radicals $R_1$ to $R_5$ are as hereinbefore defined. The oxazolidine is obtained through reaction of an alkylamino-β-hydroxyamine with an acrylic or methacrylic compound, monofunctional with regard to the double bond, and subsequent ring formation, for example with formaldehyde, according to the following reaction mechanism:

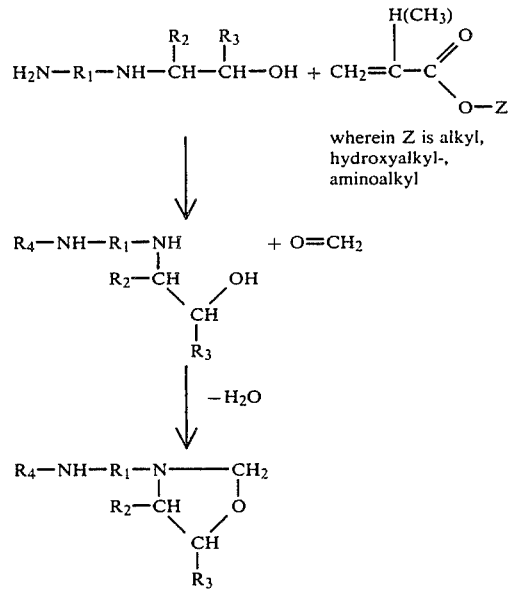

wherein Z is alkyl, hydroxyalkyl-, aminoalkyl

The preferred alkylamino-β-hydroxyamines are the commercially available products such as aminoethylethanolamine ($NH_2$—$(CH_2)_2$—$NH$—$(CH_2)_2$—$OH$) or aminopropylethanolamine or aminoethylisopropanolamine. Suitable acrylic or methacrylic monomers are, in addition to the homologous esters of acrylic or methacrylic acid with monoalcohols, monomers carrying tertiary amine groups such as dimethylaminoethylacrylate and its homologues or the homologues of hydroxyalkylacrylates. The preparation of the oxazolidine amines used according to the present invention is carried out in the first step by slowly adding the acrylic monomer to the charged amine while cooling to 30° to 50° C. The reaction is completed at from 70° to 90° C. over a time of 1 to 3 hours. When using methacrylic monomers it is advantageous to raise the temperature to about 140° C. during this phase of the reaction. Ring formation with the carbonyl compound forms at from 80° to 115° C., the reaction water which is formed being distilled off with the aid of an azeotropic entraining agent such as an aliphatic hydrocarbon having a boiling range of from between about 80° and about 120° C.

Components (A) and (B) are reacted in a MICHAEL-addition reaction at 50° to 100° C. within from 1 to 3 hours. Reaction steps (A) and (B) may be carried out in one step, in which case the addition of a catalyst for the KNOEVENAGEL-reaction is not necessary.

In step (C) the MICHAEL-addition product of components (A) and (B) is reacted with the isocyanate group of a di- or polyisocyanate via the active methylene group of the oxazolidine ring. One mole of the intermediate of (A) and (B) is reacted with one isocyanate group. The reaction is carried out in order that the isocyanate is added to the MICHAEL-addition product at 35° to 45° C. within a time period of about 1 hour. The temperature is held until all isocyanate groups have reacted.

The basic resins suitable for combination with the crosslinking components prepared according to the present invention are resin carrying a sufficient number of esterifiable groups or groups capable of amidification to guarantee sufficient crosslinking of the paint film. A large number of resins of this type are described in EP-A1 No. 00 12 463 or in AT-PS No. 372,099. The preferred resins are based on epoxy resins. Particularly preferred for cathodic deposition are the epoxy resin amine adducts which may optionally be modified for inner flexibilization.

The hardener components prepared according to the invention are employed at a level of from 15 to 40% by weight. For the individual case, the level is substantially governed by the number of functional groups available in the basic resin which are capable of transesterification reactions or amidification reactions with the carboxy groups being set free at elevated temperature.

Processing of the binder systems to provide water-dilutable coating compositions, i.e., neutralization with acids, dilution to the concentration for application or, as in most cases, co-employment or pigments and extenders, and possible methods of application are known to those skilled in the art. A preferred method of application of the coating compositions containing the hardener component of the present invention is cathodic electrodeposition (CED), whereby the object to be coated is wired as the cathode of the system.

The following examples illustrate the invention without limiting its scope. Quantities and weight units, unless otherwise stated, refer to the resin solids content of the components.

The following abbreviations are used in the examples:
DEA—Diethylamine
DOLA—Diethanolamine
DIPA—Diisopropanolamine
DEAPA—Diethylaminopropylamine
DETA—Diethylenetriamine
AEEA—Aminoethylethanolamine
APEA—Aminopropylethanolamine
BUAC—Butylacrylate
EHA—2-Ethylhexylacrylate
EMA—Ethylmethacrylate
MDE—Diethylmalonate
ACE—Ethylacetoacetate
CEE—Ethylcyanoacetate
CHX—Cyclohexanone
FA—Paraformaldehyde (91%)
BZA—Benzaldehyde
SA—Salicylaldehyde
TDI—Toluylenediisocyanate (available isomer blend)
IPDI—Isophoronediisocyanate
HMDI—1,6-Hexamethylenediisocyanate
HEOX—N-hydroxyethyloxazolidine
MGL—Ethyleneglycolmonomethylether
EGL—Monoethyleneglycolmonoethylether
DEGM—Diethyleneglycoldimethylether
MIBK—Methylisobutylketone
PSA—o-phthalic acid anhydride
THPSA—Tetrahydrophthalic acid anhydride
TOFS—Talloil fatty acid
INS—Isononanoic acid
EH—2-ethylhexanol mM Millimol The basic resins used in the examples are prepared the following way:

(BH I): A reaction vessel equipped with stirrer, thermometer and reflux condensor is charged with 1000 g of an epoxy resin (based on bisphenol A; epoxy equivalent weight ca. 500) and dissolved at 60° to 70° C. in 512 g of EGL. Then, 37 g of DEA and 158 g of DOLA are added, and the batch is reacted for 3 hours at 100° C. The product has a hydroxyl value of 375 mg KOH/g.

(BH II): 380 g of an epoxy novolak resin (epoxy equivalent ca. 190) are dissolved in 354 g of DEGM and are reacted at 80° C. with 269 g of a semiester of THPSA and HEOX, and further with 37 g of DEA and 140 g of TOFS to an acid value of below 3 mg KOH/g. 10 mM of acetic acid per 100 g of resin solids are added, and the resin is stirred for 3 hours at 65° C. The product has a hydroxyl value of 270 mg KOH/g.

(BH III): To a solution of 1000 g of an epoxy resin (based on bisphenol A; epoxy equivalent ca. 500) in 551 g of MIBK, 168 g of INS, 53 g of DOLA and 33 g of DEAPA are added at 70° C., and the reaction blend is held at 95° to 100° C. until an acid value of below 3 mg KOH/G is attained. The product has an hydroxyl value of 270 mg KOH/g.

(BH IV): 400 g of an epoxy resin (based on bisphenol A; epoxy equivalent ca. 200) are dissolved in 261 g of MGL and reacted at 90° to 95° C. with 278 g of a semiester of PSA and EH, 67 g of DIPA and 37 g of DEA, until an acid value of less than 3 mg KOH/g is attained. The product has an hydroxyl value of 230 mg KOH/g.

(BH V): 1000 g of an epoxy resin (based on bisphenol A; epoxy equivalent ca. 500) are dissolved in 663 g of MIBK and reacted at 60° C. with 267 g of a diketimine of 1 mole of DETA and 2 moles of MIBK, as well as with 280 g of TOFS and reacted further at 75° to 80° C. until an acid value of below 3 mg KOH/g is reached. The product has an hydroxyl value of 145 mg KOH/g.

The oxazolidine compounds (component (B)) are prepared in order that while cooling to 30° to 35° C., the acrylate is added within one hour to the charged amine and the reaction is completed at 70° to 90° C. (when using methacrylates the temperature should be at about 140° C.) within a time period of from 1 to 3 hours then, at 70° to 80° C., the carbonyl compound and the solvent such as special benzine with a boiling range of from 80° to 120° C. or a similar aliphatic hydrocarbon, for the solvent cook are added and the reaction is completed at 80° to 115° C. with azeotropic entraining of the reaction water. Thereafter, the solvent is vacuum-stripped.

Component (A) is prepared by reacting the C-H-acidic ester with the carbonyl compound at 80° to 150° C., the reaction water being eliminated with the aid of an entraining agent such as the special benzine mentioned above.

EXAMPLES 1-6 OF THE INVENTION

Table 1 lists the weights and reaction conditions for preparing the starting components and the hardener components according to the invention. It is advantageous to prepare the oxazolidine compound (component (B)) in the first step and to add component (A) by reacting at 50° to 100° C. for 1 to 3 hours. The KNOEVENAGEL-condensation and the MICHAEL-addition, however, may be carried out in a joint reaction. In this method the C-H-acid ester and the carbonyl compound are added to the oxazolidine compound. The reaction is carried out at 80° to 130° C. with azeotropic entraining of the reaction water. Thereafter the reaction product of (A) and (B) is reacted with the di- or polyisocyanate, the number of isocyanate groups being equivalent to the methylene groups available in the oxazolidine ring. The reaction is carried out at 35° to 45° C., optionally in the presence of an inert solvent such as xylol, or MIBK. It is advantageous to add the isocyanate within a time period of from about 45 to 90 minutes. The reaction is finished when the isocyanate value has fallen to practically zero.

TABLE 1

| | COMPONENT (A) | | | COMPONENT (B) | | | | COMPONENT (C) | |
|---|---|---|---|---|---|---|---|---|---|
| Example | C—H—Acidic ESTER | CAR-BONYL-Compound | REACTION-Conditions hrs/°C. | AMINE | ACRYLIC MONOMER | REACTION-Conditions hrs/°C. | ALDE-HYDE | DIISO-CYANATE | REACTION-Conditions hrs/°C. |
| 1 | 320 MDI | 200 MIBK | 8/145 | 208 AEEA | 256 BUAC | 2/70 | 212 BZA | 222 IPDI | 2/45 |
| 2 | 320 MDE | 66 FA | 6/120 | 208 AEEA | 368 EHA | 2/70 | 66 FA | 174 TDI | 1/40 |
| 3 | 226 CEE | 196 CHX | 6/130 | 236 APEA | 228 EMA | 2/140 | 212 BZA | 168 HMDI | 2/35 |
| 4 | 226 CEE | 66 FA | 7/125 | 208 AEEA | 256 BUAC | 2/70 | 244 SA | 174 TDI | 1/40 |
| 5 | 260 ACE | 200 MIBK | 9/140 | 236 APEA | 368 EHA | 2/75 | 66 FA | 222 IPDI | 2/45 |
| 6 | 260 ACE | 66 FA | 8/125 | 208 AEEA | 228 EMA | 2/140 | 66 FA | 174 TDI | 1/40 |

The hardener components prepared according to Examples 1 to 6 of Table 1 are combined with basic resins to give coating compositions by thoroughly mixing the components and subsequent neutralization with acids, preferably formic acid, until the desired dilutability with water is attained. Prior to dilution with deionized water, optionally pigments and extenders and/or catalysts are dispersed in the resin blend. These operational steps may be carried out prior to the addition of the acid or with the individual components.

Examples of binder systems based on the products prepared as described above are listed in Table 2.

TABLE 2

| Basic Resin parts resin | Hardener Component parts resin solids | Formic Acid millimoles/1000 g | pH Value 10% solution |
|---|---|---|---|
| 70 BH I | 30 Example 4 | 40 | 6.3 |
| 80 BH I | 20 Example 2 | 45 | 6.1 |
| 65 BH II | 35 Example 5 | 35 | 6.7 |
| 80 BH III | 20 Example 1 | 40 | 5.8 |
| 70 BH III | 30 Example 3 | 50 | 5.6 |
| 75 BH IV | 25 Example 6 | 45 | 6.0 |
| 80 BH V | 20 Example 2 | 55 | 6.2 |

The coating compositions are diluted with water to application viscosity, optionally after combination with pigments and extenders and/or catalysts and optionally co-employing auxiliary solvents. The films, cured at 160° to 180° C., exhibit excellent performance regarding mechanical properties and resistance to corrosive substances. Particularly on cathodic deposition according to the CED process, primers with particularly favorable characteristics can be obtained.

As will be apparent to one skilled in the art, various modifications can be made within the scope of the aforesaid description. Such modifications being within the ability of one skilled in the art form a part of the present invention and are embraced by the appended claims.

It is claimed:

1. A water-dilutable cationic paint binder comprising (a) from 60 to 85% by weight of a synthetic resin which will undergo neutralization with an acid, contains functional groups which are esterifiable or capable of amidification and which is water dilutable after at least partial neutralization with an acid, and (b) from 15 to 40% by weight of a hardener compound which crosslinks at elevated temperature with said functional groups of (a) through esterification or amidification and which comprises (A) a KNOEVENAGEL (COPE) reaction product at an elevated temperature of a carbonyl compound and a compound of the general formula

wherein
X is —COOR, —CN or —COCH$_3$,
Y is —COOR, and
R is an alkyl radical having from 1-4 C-atoms, reacted at an elevated temperature in a MICHAEL-addition reaction with (B) a substituted oxazolidine carrying a secondary amino group and having the general formula